(12) United States Patent
Gombrich et al.

(10) Patent No.: US 6,475,164 B2
(45) Date of Patent: Nov. 5, 2002

(54) PHYSICIAN'S COLLECTOR

(75) Inventors: Peter P. Gombrich, Chicago; Richard A. Domanik, Libertyville, both of IL (US); George Gorodeski, Beechwood, OH (US)

(73) Assignee: Ampersand Medical Corporation, Chicago, IL (US)

( * ) Notice: Subject to any disclaimer, the term of this patent is extended or adjusted under 35 U.S.C. 154(b) by 0 days.

(21) Appl. No.: 09/725,332

(22) Filed: Nov. 29, 2000

(65) Prior Publication Data

US 2001/0023321 A1 Sep. 20, 2001

Related U.S. Application Data

(60) Provisional application No. 60/167,831, filed on Nov. 29, 1999.

(51) Int. Cl.[7] .............................................. A61B 10/00
(52) U.S. Cl. ..................... 600/569; 600/572; 604/328
(58) Field of Search ................................ 600/562, 569, 600/570, 571, 572; 606/160; 604/1, 328, 330, 385.01, 385.12, 385.17, 509, 264, 271

(56) References Cited

U.S. PATENT DOCUMENTS

| 3,664,328 | A | | 5/1972 | Moyle, Jr. et al. | ........... 600/569 |
|---|---|---|---|---|---|
| 4,467,816 | A | * | 8/1984 | Schluter et al. | ............. 600/569 |
| 4,633,886 | A | | 1/1987 | Bucaro, Jr. | .................. 600/562 |
| 5,231,992 | A | | 8/1993 | Leon | ........................... 600/572 |
| 5,391,179 | A | * | 2/1995 | Mezzoli | ....................... 606/196 |
| RE35,312 | E | * | 8/1996 | Christoudias | ............... 600/207 |
| 5,649,902 | A | * | 7/1997 | Yoon | .............................. 604/1 |
| 5,741,648 | A | | 4/1998 | Hemstreet, III et al. | ........ 435/6 |
| 5,919,145 | A | * | 7/1999 | Sahyatjian | ................... 600/572 |
| 6,004,260 | A | * | 12/1999 | Thompson | ................... 600/33 |

FOREIGN PATENT DOCUMENTS

| DE | 28 29 118 | 1/1980 |
|---|---|---|
| GB | 2 341 321 | 3/2000 |
| WO | WO 85/00100 | 1/1985 |
| WO | WO 88/05908 | 8/1988 |
| WO | WO 91/16004 | 10/1991 |

OTHER PUBLICATIONS

R.H.C. Benthall, 1969, *The Lancet*, 574–575, "Suction Amnioscope".
Evans et al., 1969, *Acta Cytologica*, 13:119–121, "A Membrane Cytologic Technique for Assessing the Extent of Ectocervical Carcinoma Using the Tenovus Applicator".
International Search Report for PCT/US00/32504.

* cited by examiner

*Primary Examiner*—Kevin Shaver
*Assistant Examiner*—Charles Marmor, II
(74) *Attorney, Agent, or Firm*—Merchant & Gould P.C.

(57) ABSTRACT

Cervical cells can be sampled in such a way as to retain the spatial relationships that existed between the cells prior to sampling. The cells can be collected by using a cervical cell collector that samples a cervix in a spatially resolved manner. The cervix is sampled by placing a sampling balloon in position adjacent to a cervix and inflating the sampling balloon to force a sampling surface of the sampling balloon into contact with the cervix, thereby transferring cervical cells from the cervix to the sampling surface of the sampling balloon. The sampling balloon is then deflated and withdrawn. Then, the adhered cervical cells are treated with a marker and are optically analyzed.

4 Claims, 10 Drawing Sheets

PHYSICIAN'S COLLECTOR

RELATED APPLICATIONS

This application claims priority to provisional application Serial No. 60/167,831, filed Nov. 29, 1999, entitled "CERVICAL TISSUE SAMPLE COLLECTOR HAVING A FLUID DISPENSER AND CONTAINER", which is specifically incorporated by reference herein.

TECHNICAL FIELD

The invention relates generally to cervical cell sampling and more specifically to devices and methods whereby cervical cell samples can be quickly and easily attained while retaining the spatial arrangement of the cervical cells.

BACKGROUND

Cervical cancer is a leading form of cancer among women. In the United States alone, there are believed to be more than two million cases of precancerous cervical abnormalities annually. The U.S. also sees, on average, about sixty five thousand cases of cervical carcinoma and about sixteen thousand cases of invasive cervical cancer. Although screening is less common outside the Unites States, nearly half a million cases of cervical cancer are detected each year around the world.

Cervical cancer frequently begins as a precancerous lesion of the cervix. These lesions are also known as cervical intraepithelial neoplasia. If left untreated, these lesions can deepen over time and ultimately develop into an invasive cancer of the cervix and associated tissues. Fortunately, early detection followed by appropriate treatment results in a very high cure rate for cervical cancer.

Therefore, it is quite important that at least certain factions of the female population undergo regular screening. These factions include patients with previous cervical abnormalities and those who have a family history of cervical abnormalities. Women who are sexually active are at greater risk and should undergo regular screening, as are those who test positive for HPV (human papillomavirus). This is a sexually transmitted virus that in some forms can cause genital warts.

During the 1940's, Dr. George Papanicolaou developed a screening test which bears his name and which has become the most widely used screening technique for detecting abnormal cervical cells. Today, this test is known more commonly as the PAP test or the PAP smear test. Typically, the PAP test is performed in the physician's office as part of a woman's routine gynecological examination. The test involves collecting cervical cells via a brush, stick or swab that is used to loosen and then collect cells that can be examined microscopically.

Cervical samples taken for the purposes of Pap testing are deposited on a planar microscope slide, fixed to prevent cell loss or degradation, and stained in a manner that accentuates and differentiates the various cellular structures. These prepared samples are subjected to detailed microscopic evaluation by a cytotechnologist or pathologist to detect and classify any cellular abnormalities that may be present in the cells deposited on the microscope slide. The results of these evaluations are reported to the attending physician who determines whether additional evaluation or treatment of the patient is required.

The Pap test as it is currently practiced is time consuming and requires a highly skilled supporting infrastructure. Even in countries with the necessary infrastructure, several weeks can elapse between taking the sample and reporting the results of the evaluation to the attending physician. The uncertainty attendant in this delay is stressful to the patient. As it is not practical for the patient to be retained at the medical facility until the results of the evaluation have been returned, it is necessary for the attending physician to contact the patient to inform them that the results of the test were negative or, conversely, if the results were positive, to arrange for a follow-up visit.

In the US, fewer than 60% of the patients contacted with positive results actually present themselves for follow-up evaluations or treatment. This percentage is lower in other countries and is particularly low in public health screening programs and clinics that deal predominantly with transient populations and populations that are remote from the site of testing. Furthermore, depending upon the particular patient population, between 50 and 90 percent of all Pap samples taken are determined to contain no evidence of cellular abnormalities. This high percentage of negative samples imposes a substantial burden on the health care system and diverts resources from making cervical screening tests more widely available.

It is therefore desirable to provide a means of cervical screening that can produce a determination of whether a sample does or does not contain evidence of cellular abnormalities within the time frame of a typical cervical examination. As such a means provides the test results before the patient leaves the examination area, the uncertainty and stress of waiting for a negative diagnosis is eliminated and patients showing positive results can be retained for immediate follow-up and treatment.

Identifying those patients showing no signs of cellular abnormalities at the time of the initial examination also reduces the number of samples that must be sent to a laboratory for evaluation. This reduces the non-productive burden on the health care system and frees resources that can be used to increase the availability of cervical screening and other diagnostic testing.

The manner in which a positive result is followed up varies substantially by country In some countries such as the US, a finding of ASCUS or higher is generally considered to be grounds for follow-up or medical intervention. In other countries, the standard of care is to follow up or intervene in cases where the detected degree of abnormality corresponds to LSIL (or HSIL) and higher, but, in recognition that many lower grade abnormalities are benign or revert to normal over time, to ignore lower grade detected abnormalities. It is therefore desirable to be able to establish a reporting threshold that is consistent with the prevailing standard of care.

Cervical abnormalities generally present in the form of lesions or localized clusters of abnormal cells. The sampling methods utilized in current cervical screening procedures acquire cells from these lesions, but then disperse these cells into a typically much larger number of normal cells obtained from outside of the boundaries of the lesion. This dispersion results in the evaluation of a conventional cervical sample being an exercise in the detection of a rare event, that is, finding one or a few abnormal cells within a background consisting of a very large number (50,000–300,000) of normal cells. Dispersion also precludes using the sample to determine the location of the lesion on the cervix.

It is therefore desirable that a means of sampling and evaluation be provided that retains the spatial relationships that exist between the cells in-vivo. Retaining these relationships effectively eliminates dispersion and allows mapping of the test results onto the cervix for the purpose of guiding follow-up or intervention.

SUMMARY

Accordingly, the invention is directed towards means and methods for sampling cervical cells in such a way as to retain the spatial relationships that existed between the cells prior to sampling.

In a preferred embodiment, the invention is found in a cervical cell collector that includes sampling means for sampling a cervix in a spatially resolved manner, supporting means for supporting the sampling means, and inflation means for reversibly inflating and deflating the sampling means.

In another preferred embodiment, the invention is found in a method of sampling and analyzing cervical cells while maintaining the spatial orientation of the cervical cells. The method includes placing a sampling balloon in position adjacent to a cervix and inflating the sampling balloon to force a sampling surface of the sampling balloon into contact with the cervix, thereby transferring cervical cells from the cervix to the sampling surface of the sampling balloon. The sampling balloon is then deflated and withdrawn. Then, the adhered cervical cells are treated with a marker and are optically analyzed.

Other features and advantages of the present invention will be apparent from the following detailed description and drawings.

DETAILED DESCRIPTION OF THE PREFERRED EMBODIMENTS

Figure 1:
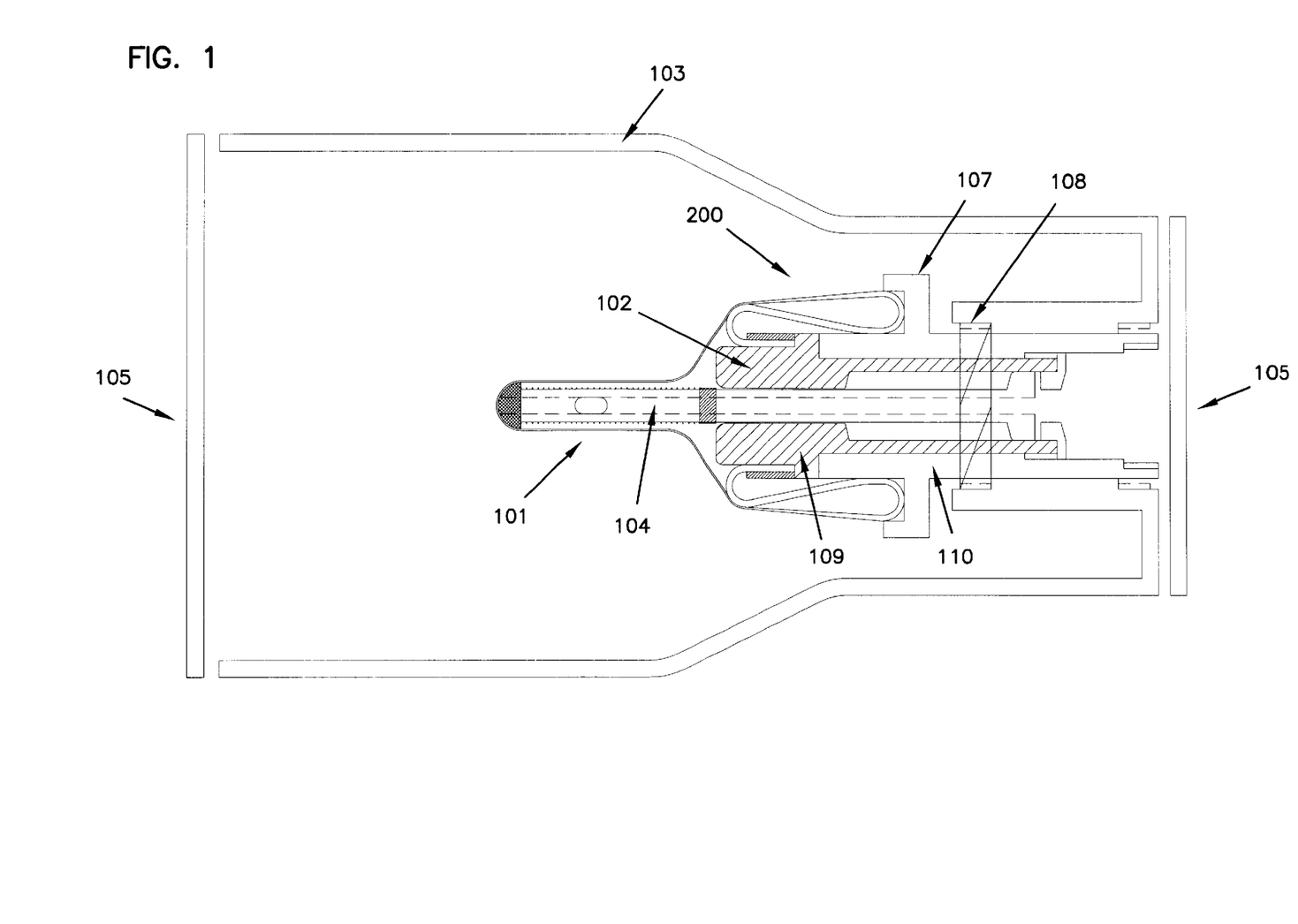
FIG. 1 is a sectional view of a physician's collector in accordance with a particular embodiment of the present invention. This Figure shows the compliant cell sampling member in a folded state prior to use.

The present invention is best understood with reference to the Figures, in which similar reference numbers are used to refer to similar elements in multiple Figures. FIG. 1 shows a particular embodiment of the present invention. The physician's collector includes a compliant cell sampling member 101 that is attached to an interface element 102 and that is mounted within a multifunctional container 103. A stylette 104 passes through the interface element 102 and into the cell sampling member 101 where it is bonded to the interior of the tip of the cell sampling member 101.

When the physician's collector is delivered to a clinician, it is preferred that the ends of the multifunctional container 103 be closed by suitable covers 105 that can be held in place by a shrinkable sleeve that incorporates a perforated tear strip (not illustrated). If desired, human and machine readable labeling such as a serial number of the physician's collector, expiration date and other relevant data can be provided on an exterior surface of the physician's collector.

The sampling member 101 as illustrated in FIG. 1 is preferably a balloon structure 200 that is made of a suitable elastomeric material such as silicone rubber, latex rubber, polyurethane or a thermoplastic elastomer. Alternatively, the sampling member 101 can include a compliant solid body such as a graded density foam. For the balloon embodiment, the wall thicknesses and other parameters are controlled during fabrication to obtain a desired pliability. In a preferred embodiment, the balloon structure is created using an injection molding process or similar process that provides for the preferred control over local wall thickness.

Figure 2:
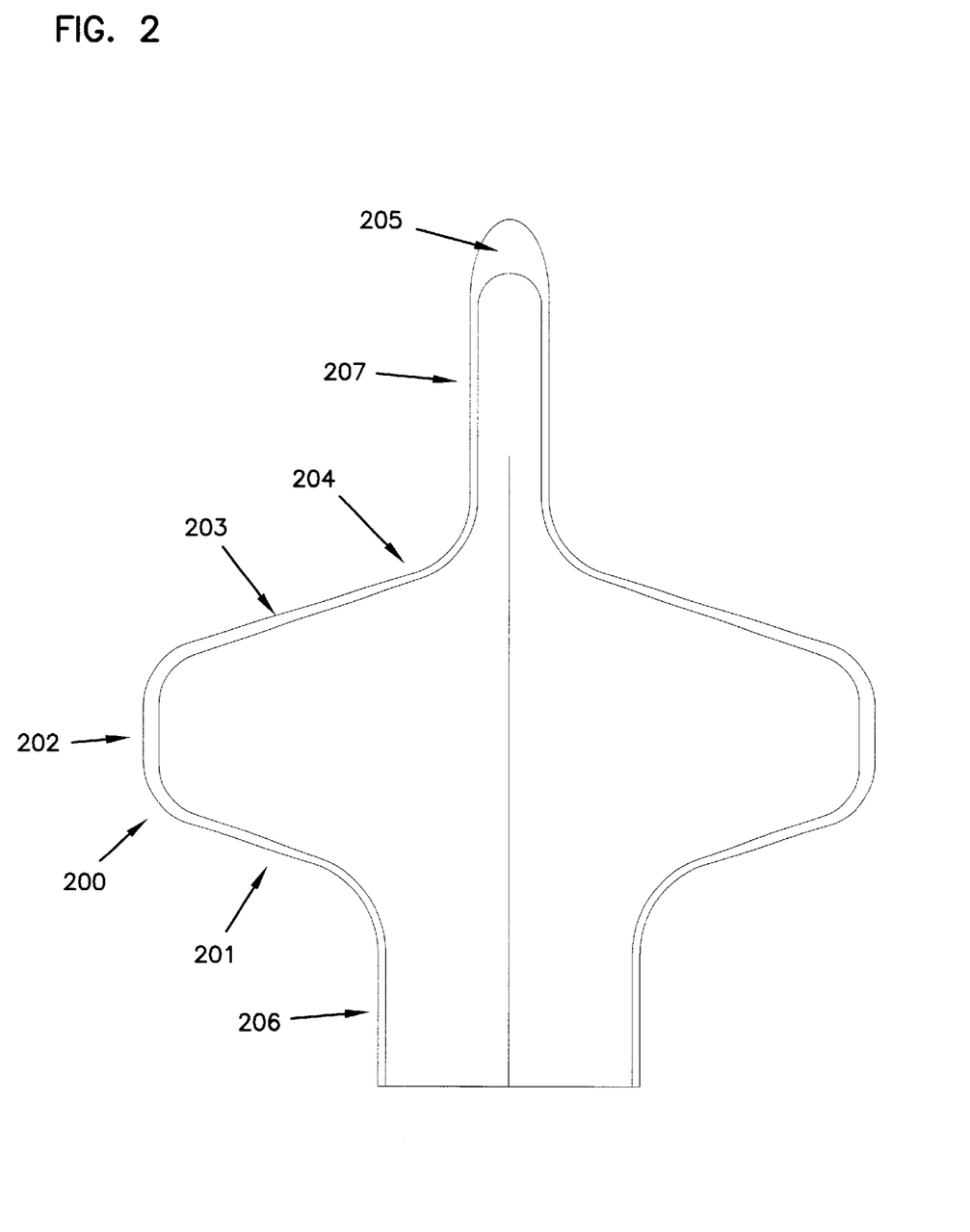
FIG. 2 is a sectional view of a compliant cell sampling member, illustrating the relative wall thicknesses of the sampling member in accordance with a particular embodiment of the present invention.

FIG. 2 provides an example of a balloon 200 in which the wall thicknesses vary with position. Preferably, the rear walls 201 and the side walls 202 have a relatively constant thickness that is greater than the rest of the balloon 200. The front wall 203 preferably tapers from a maximum thickness at the side wall 202 to a minimum value at the root 204 of the tip of the structure 200. Preferably, this minimum thickness is employed over most of the length of the tip of the balloon 200 where the thickness is again increased. In a particular embodiment, the neck 206 of the balloon 200 is also thinner than the rear wall 201.

Each wall thickness variation illustrated in FIG. 2 is intended to impart specific behavioral and performance properties to the balloon 200. For example, the substantial thickening at the tip 205 is intended to facilitate insertion of the tip into the cervical canal and to provide an anchoring site for the stylette 104. Further, the thick rear wall 201 and side walls 202 function as a spring that helps drive the deployment of the sampling member 101 from its folded state. Moreover, the thick rear and side walls 201, 202, respectively, help provide the stiffness beneficial in communicating forces from the handle 301 to the sampling member 101 and to resist expansion when air is introduced into the balloon 200. The sampling member 101 can be biased to an inflated sampling configuration, or the sampling member 101 can be biased to a deflated insertion and removal configuration.

The thick side walls 202 provide a ring that causes the thinner front wall 203 to drape over the cervix when the tip region 207 of the balloon structure 200 is constrained by the cervical canal and the ring is brought into contact with the cervix by pressure applied via the handle 301. The angle between the front wall 203 and the axis of the balloon is preferably chosen to minimize the change in the area of the front wall 203 that occurs during the draping process and thus to minimize the potential for forming wrinkles in the draped front face. Reducing the wall thickness in the tip region 207 allows this region to selectively expand when air is introduced while the reduced wall thickness in the neck region 206 facilitates removal of the balloon 200 from its mold.

While not explicitly illustrated, additional local variations in wall thickness can be implemented to achieve additional specific behavioral and performance characteristics in the balloon 200. Also not shown is a small flange that projects outward from the periphery of the side wall 202. This flange adds stiffness to the side wall 202, serves as a grip point when used with particular embodiments of an interface element 102, and provides a fluid seal in an embodiment of the present invention wherein a reagent is added to the multifunctional container 103 after cell collection has been completed.

Figure 9:
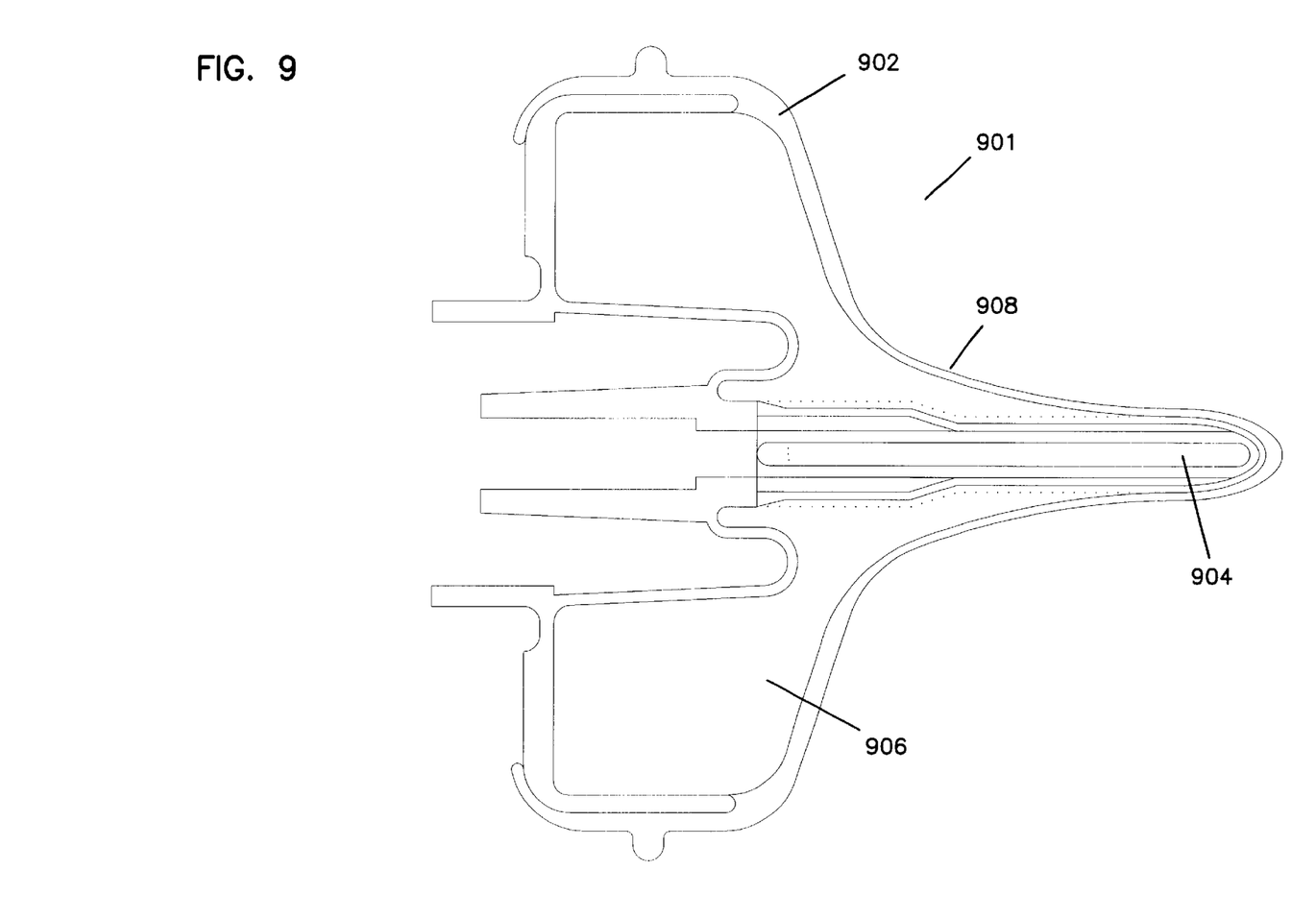
FIG. 9 is a sectional view of another embodiment of the sampling member in accordance with the present invention.

In another embodiment, the balloon 200 can include both an inner portion and an outer portion, as illustrated in FIG. 9. This Figure shows a balloon 901 that has both an inner balloon 906 and an outer balloon 902, as well as a stylette 904. It has been found that this particular embodiment can, in certain circumstances, provide additional control over inflation and deflation, as well as better control over the shape and configuration of the sampling surface 908. In one embodiment, only the inner balloon 906 is inflated or deflated, while in another embodiment, both inner and outer balloons 906 and 902, respectively, can be inflated or deflated either in combination or separately.

Figure 4:
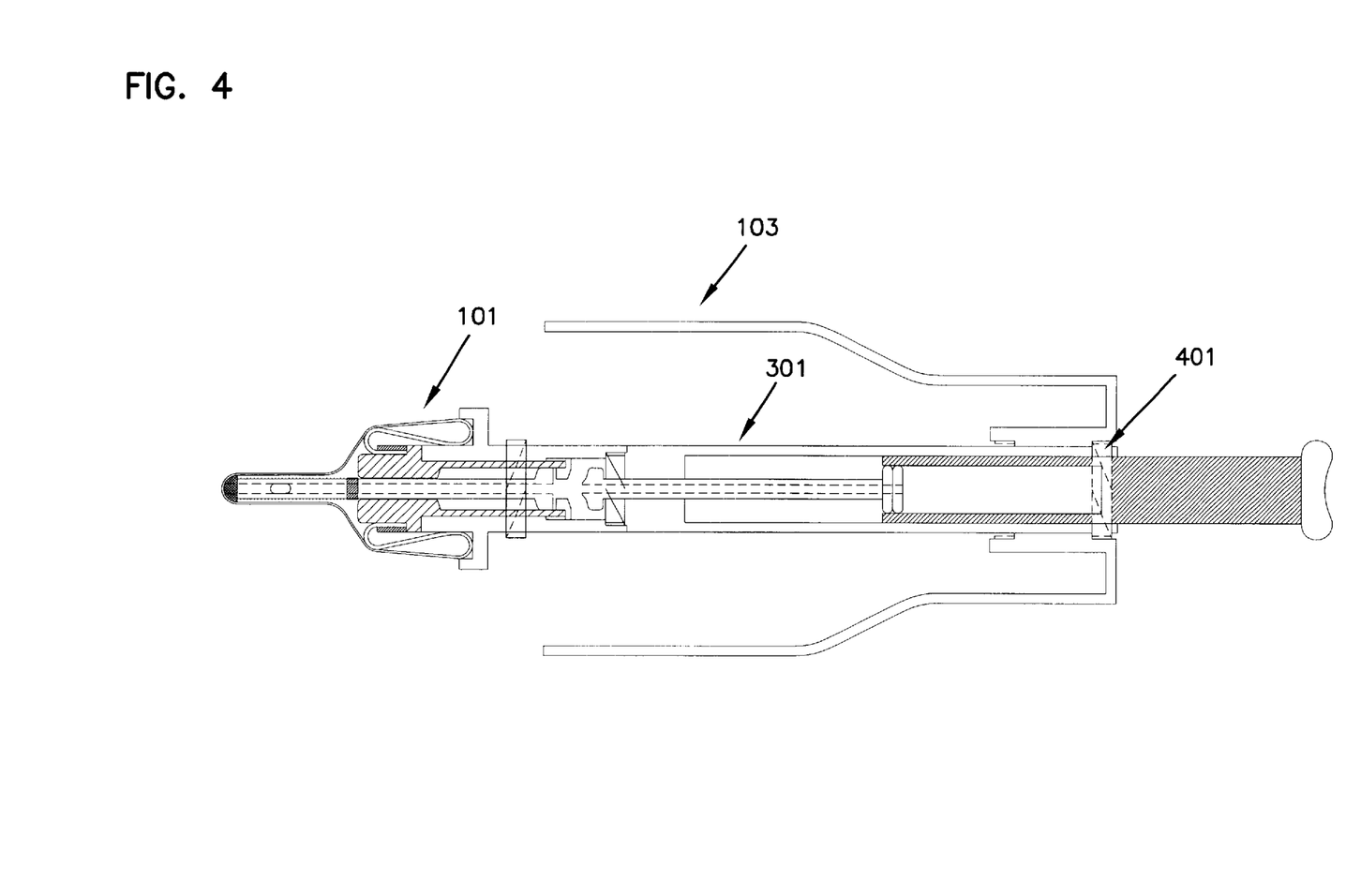
FIG. 4 is a sectional view of the physician's collector of FIG. 1, with the container positioned at the end of the handle.

When the container 103 is released from the interface element 102, it can be slid to the opposite end of the handle 301 where it is retained in position by mating latching features 401. These are illustrated schematically as a quarter turn right-hand threaded male-female fastener pair, although other retention means such as snap latches can be employed for this function. These mating latching features 401 are configured such that once the container 103 is secured to the handle 301, the container 103 assumes a predefined rotational orientation with respect to the folded sampling member 101. The container 103, when secured at the end of the handle 301, forms a finger grip that can be held by the clinician. Preferably, the modified diamond shape of the end section of the container 103 is such that when naturally gripped by either a right or left handed clinician, the folded sampling member will assume a predefined rotational orientation with respect to the cervix into which it is to be inserted. Alignment marks, not shown, on the container 103 and handle 301 further encourage and guide the clinician to present the device to the cervix in this orientation.

As suggested by FIGS. 5A–5D, the clinician guides the device through a speculum into the vagina and inserts the tip of the sampling member 101 into the cervical canal 501 until the shoulder of the sampling member 101 seats against the cervix. See FIG. 5A. The flattened shape of the sampling member affords the clinician improved visibility of the cervix during insertion, while the bullet shaped tip of the sampling member and the stiffness imparted by the stylette 104 facilitate insertion of the sampling member 101 into the cervical canal 501.

Figure 5A:
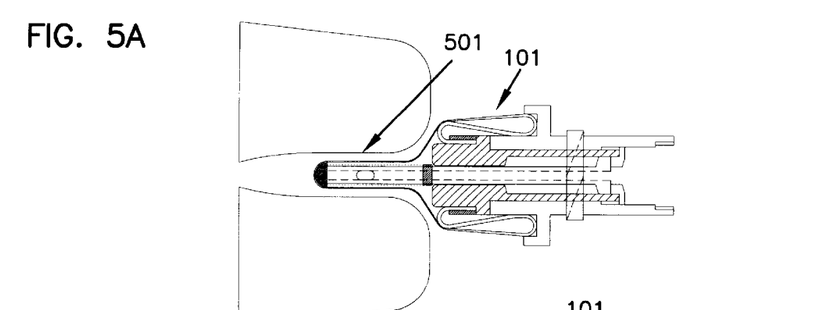
FIGS. 5A–D are sectional views of the physician's collector of FIG. 1, illustrating the use of the physician's collector in sampling cervical cells.

Preferably, the stylette 104 is constructed of a compliant material such as low density polyethylene in a tubular form that provides adequate stiffness to aid in the insertion, but which can flex to avoid injury to the patient should the tip be misaligned with the cervical canal or should excessive force be applied during insertion. The stylette 104 can be a rigid floating member. The tubular nature of the stylette 104 also provides a means for introducing air into the sampling member 101 during the sampling process.

Figure 5B:
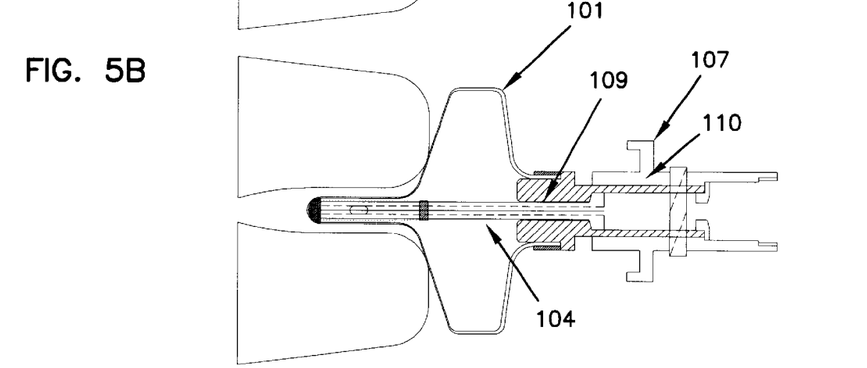

Insertion of the tip of the sampling member 101 into the cervix proceeds until the body of the sampling member 101 is properly seated against the mouth of the cervix, the sampling member 101 is deployed from its initial folded state into its unfolded sampling configuration as is shown in FIG. 5B.

Deployment is triggered partially by depressing the actuator button 303 at the end of the handle 301. The internal structure of the handle 301 can, in essence, be described as a syringe, the major elements of which consist of a barrel 304 that slides within the handle 301, an extension of which forms the actuator button 303; and a plunger 305 having an elongated hollow shaft 306 that is slideably retained in the body of the handle 301 and which makes air tight sliding contact with the interior of the barrel 304.

Figure 3:
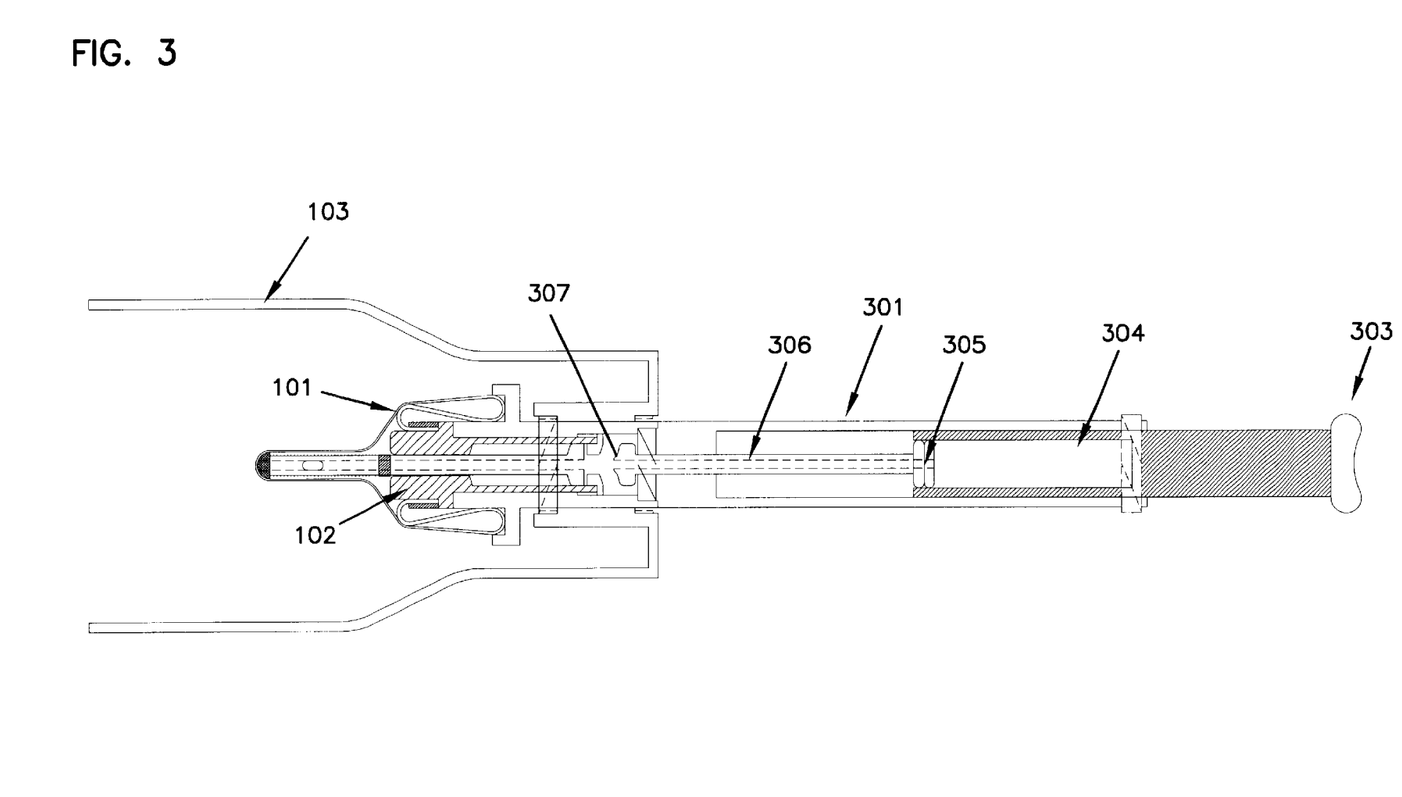
FIG. 3 is a sectional view of the physician's collector of FIG. 1, with a handle attached and a container positioned over the sampling member.
Figure 5C:
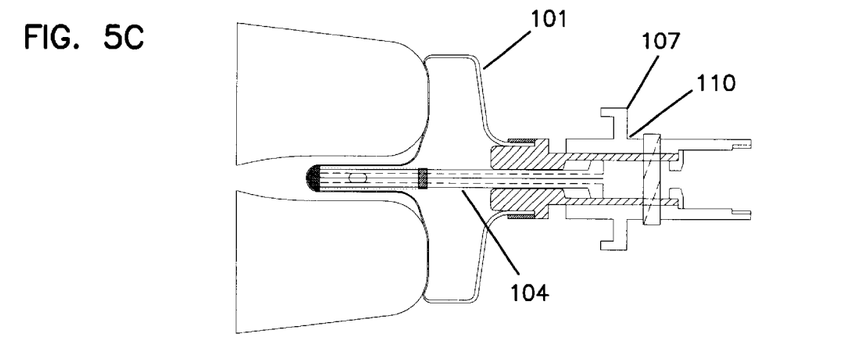

As the button 303 (FIG. 3) is initially depressed, friction between the plunger 305 and the barrel 304 causes the barrel 304, plunger 305 and hollow shaft 306 to move in unison in the direction of the sampling member 101 until the end 307 of the hollow shaft 306 makes contact with the inner portion of the interface element 102. Since the outer part of the interface element 109 is secured to the handle 301 by means of the latching features 107 and is thereby constrained from moving, continuing this motion forces the inner portion of the interface element 110 to move relative to the outer portion of the interface element 109 in the direction of the sampling member 101. This motion causes the sampling member 101 to move longitudinally with respect to the outer portion of the interface element 109 and thus to be released from the latching features 107 on the outer portion of the interface element 109. Once freed of the latching features 107, the rear wall 201 and side wall 202 of the sampling member 101 act as a spring that drives deployment of the sampling member into its unfolded state. Deployment ceases when the rear end of the stylette 104 seats against the inner surface of the inner portion of the interface element 110 forming an air tight seal. As is shown in FIG. 5C, pushing the handle toward the patient causes the side walls 202 of the sampling member 101 to move toward and ultimately to contact the surface thus draping the front wall of the sampling member 203 over the cervix. The sampling member 101 has a surface, when inflated, that approximates a endo-cervical region, as illustrated in the Figures.

The actions of inserting the tip of the sampling member into the cervical canal, deploying the sampling member and draping the front wall 203 (FIG. 5C) of the sampling member over the external cervix brings the cell collection surface of the device into substantial, but not necessarily complete, contact with those portions of the cervix from which samples are to be acquired. In particular, there are substantial variations in the shape and dimensions of the cervix and cervical canal between women which make it difficult to guarantee contact with all relevant areas when using a sampling device having fixed dimensions and shape. For this reason, the embodiment of the present invention being described utilizes selective expansion of portions of the sampling member to accommodate this range of human variability and to perfect contact between the device and the cervix to which it is applied.

This expansion is driven by the injection of air into the sampling member 101 and is controlled both by the wall thicknesses in the sampling member and by contact between the sampling member and the cervical tissue. Air is injected into the sampling member by means of the syringe structure incorporated into the handle 301. As noted earlier, the initial depression of the actuating button 303 on the handle 301 causes the barrel 304, plunger 305 and hollow shaft 306 to move in the direction of the sampling member 101 until the end of the hollow shaft 306 makes contact with the inner portion of the interface element 109. This contact causes the hollow shaft 306 to form an airtight seal with the interface element 109.

Figure 5D:
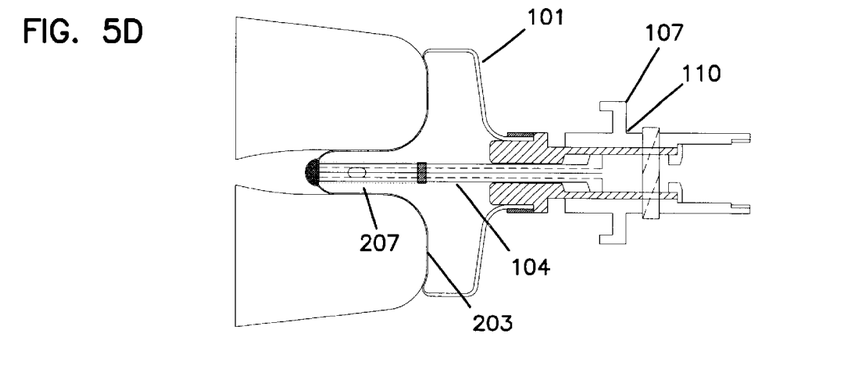

As the interface element 109 acts as a fixed stop against which the hollow shaft 306 presses, any further depression of the actuator button 303 will cause the barrel 304 of the syringe to move relative to the sealing element of the plunger 305. This relative motion causes air to be displaced through the hollow shaft 306, interface element 102 and stylette 104 into the sampling member 101 where it causes selective expansion of the front wall 203 and tip region 207 of the sampling member 101 in accordance with the constraints identified above and as is shown in FIG. 5D. As illustrated, the sampling member 101, when inflated, has a surface that is configured to approximate an endo-cervical portion of the cervix. The sampling member 101 can, when inflated, have a surface that is configured to approximate both the endo-cervical and the exo-cervical portions of the cervix.

Exfoliated cervical cells are transferred from the surface of the cervix to the surface of the sampling member 101 on contact between the surfaces. This transfer is facilitated by proper preparation of the cervix and by pre-conditioning of the sampling member. Mucus is generally present on the surface of the cervix and/or in the cervical canal. Similarly, blood and other fluids may also be present. As mucus, blood and other such extraneous materials can interfere with the evaluation of cervical samples, it is common practice to remove these extraneous materials from the cervix, typically by using a cotton swab, before a cellular sample is taken. This same convention is also practiced in conjunction with the present invention and results in a cervix that is relatively dry and free of extraneous materials.

Sampling by a contact means rather than by an abrading or scraping means as is employed by other cervical cell sampling devices confers certain benefits to the clinician. Cancerous lesions initiate at discrete foci and, except in extreme cases, are localized to specific regions of the cervix at the time of sampling. Contact sampling retains the spatial or topological relationships between the collected cells. Assuming that a lesion is present on the cervix, retention of the spatial relationships results in regions on the cell collection surface that are enriched in abnormal cells.

A co-pending application Ser. No. 60/112,274 describes a means of detecting and determining the degree of abnormality or abnormal cells on a complex surface such as is represented by the cell sampling member of the present invention. Localization of the abnormal cells on the surface of the cell collection device results in a higher signal to noise ratio between normal and abnormal cells, and thus improved detectability of abnormal cells relative to what is possible with samples obtained by an abrasive or scraping means where in the abnormal cells are dispersed throughout the sample.

Furthermore, localized sampling in conjunction with in-situ detection on the collection surface permit the locations on the cervix of any lesions detected to be presented to the clinician in a manner that directs the clinician to these specific areas of the cervix for the purposes of clinical follow-up. Detection of abnormalities in a sample obtained by abrasive or scraping means, on the other hand, requires that the clinician examine the entire cervix in order to determine the location of the lesion. Certain features of the present invention such as those that establish the orientation of the sampling member with respect to the cervix are particularly intended to support and facilitate use of the present invention in this manner.

Adhesion of exfoliated cells to the sampling member can be the result of the intrinsic properties of the materials used in the fabrication of the sampling member, or can be imparted to these materials by means of coatings or surface treatments. Many silicone rubbers, for example, exhibit an intrinsic tackiness that is capable of binding cells to the surface of the material. This is particularly true of low durometer formulations such as the GE 6030 materials available from General Electric, Waterford, N.Y. that have been cured to the minimum extent necessary to develop the required mechanical and physical properties. In addition, certain formulations of silicone rubber such as Shin Etsu 1935 available from Shincor, Akron, Ohio have been specifically formulated to have and to maintain a high level of surface tackiness.

The cell binding capability of a material can also be enhanced by surface modification or coating. For example, a variety of commercially available glow plasma or corona discharge and photochemical processes can be used to introduce charged species such as amino or carboxyl groups into the surface of the material. Such charged species are known to facilitate cell binding and, furthermore, can serve as "anchors" for the attachment of other cell binding materials to the surface. Glow discharge and photochemical processes can also be used to deposit coatings on most materials. The PhotoLink™ process offered by SurModics, Eden Prairie, Minn. is one of many such commercially available processes. Other coatings that enhance cell binding can be applied by a spray or dip process. For example, collagen fraction IV can be applied to silicone rubber from aqueous or acetic acid solution to enhance cell binding. The coating can include a silicone-based pressure sensitive adhesive.

Once the cellular sample has been collected on the surface of the sampling member 101, the device is removed from the patient. This is facilitated by releasing any air that may have been injected into the sampling member 101 during the sampling process. This can include applying a vacuum while removing the device from the patient. In the specific embodiment described here, release of the pressure being applied to the actuating button 303 allows the air pressure within the sampling member 101 to push on the syringe elements 304, 305, 306 within the handle 201 so that the entire syringe element moves away from the sampling element 101. This releases the mechanical pressure that maintains the air tight seal 601 between the hollow shaft of the plunger 306 and the interface element 109. Breaking these seals allows the escape of any air pressure within the sampling member that was not relieved by motion of the syringe element.

Figure 6A:
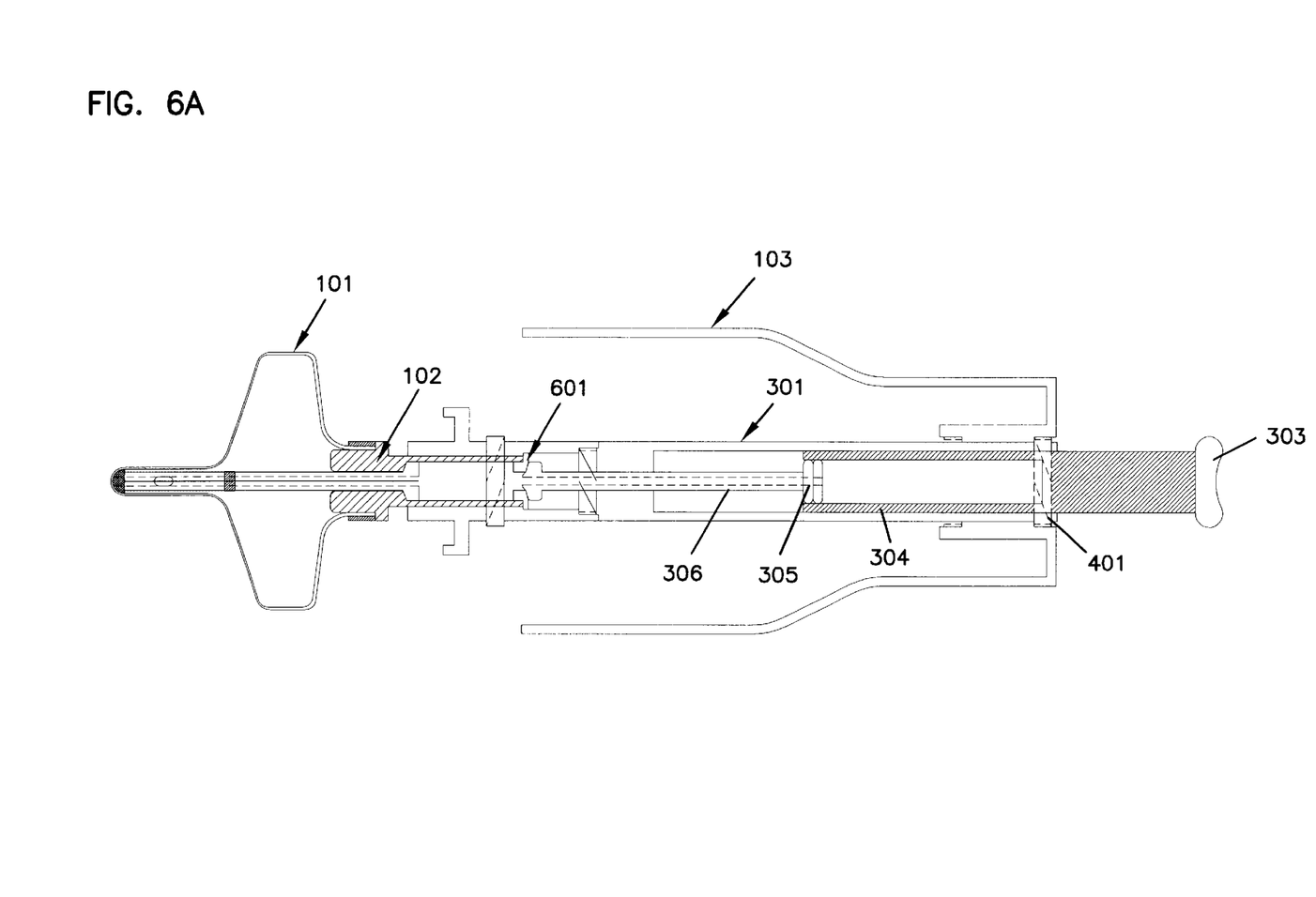
FIG. 6A is a sectional view of the physician's collector of FIG. 1, with the sampling member in an unfolded position. This corresponds to the configuration of the collector either immediately before or immediately after sample collection.
Figure 6B:
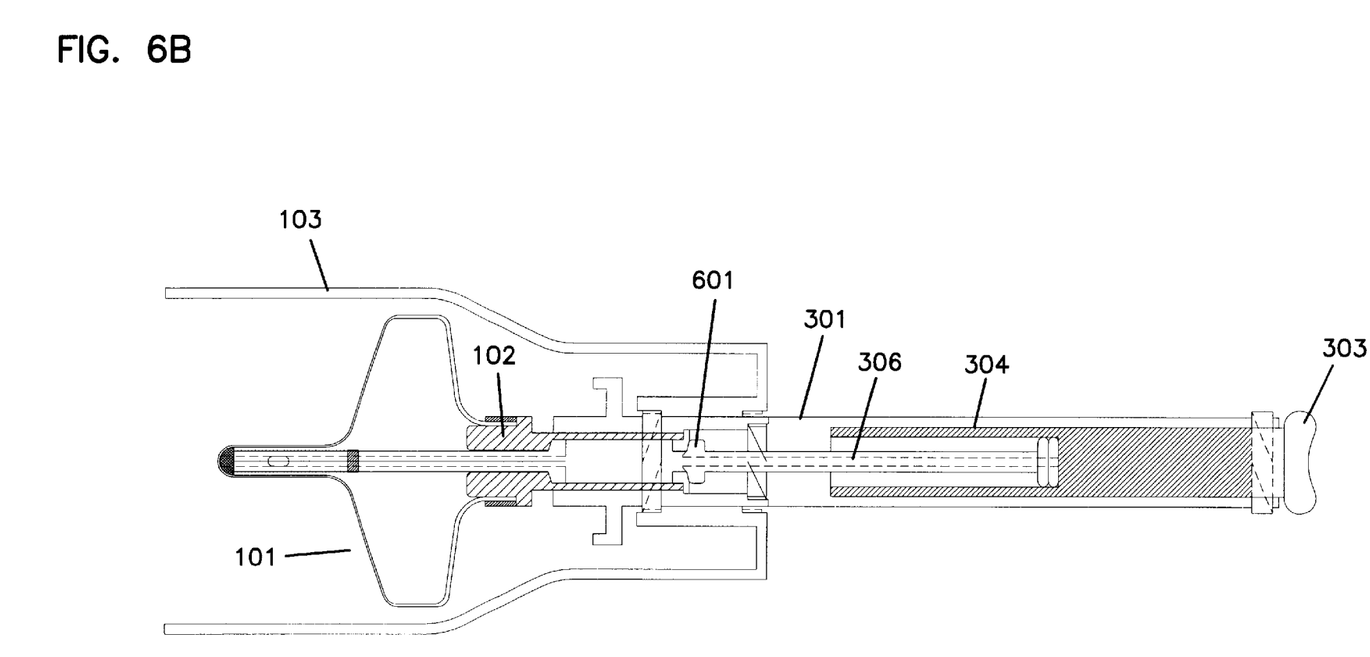
FIG. 6B is a sectional view of the physician's collector of FIG. 1, with the sampling member in an unfolded position, with the container secured over the sampling member. In this Figure, the handle has not yet been removed.

During removal of the device from the patient, the collected sample is protected from contact with the vaginal walls and other surfaces by the thickened rear 201 and side 202 walls of the sampling member. Once removed from the patient, the device is in the configuration depicted in FIG. 6A. The sample is protected by performing the reverse of the process previously described for exposing the sampling member. Specifically, the container 103 is released from the feature 401 retaining it to the handle; slid along the handle 301 until it encloses the sampling member 101; and secured to the interface element 102 by engaging the retaining features 108 between these two elements. The same motion that secures the container 103 to the interface element 102 releases the handle 301 from the interface element 102 and allows the handle 301 to be removed from the device. This places the device in the configuration shown in FIG. 6B. Using the handle 301 to guide movement of the container 103 relative to the sampling member 101 prevents the container 103 from coming into contact with the collected cells. This is in contrast to other cervical sampling devices wherein insertion of the device into a container is performed manually and thus may result in contact between the collected cells and the container.

Figure 7:
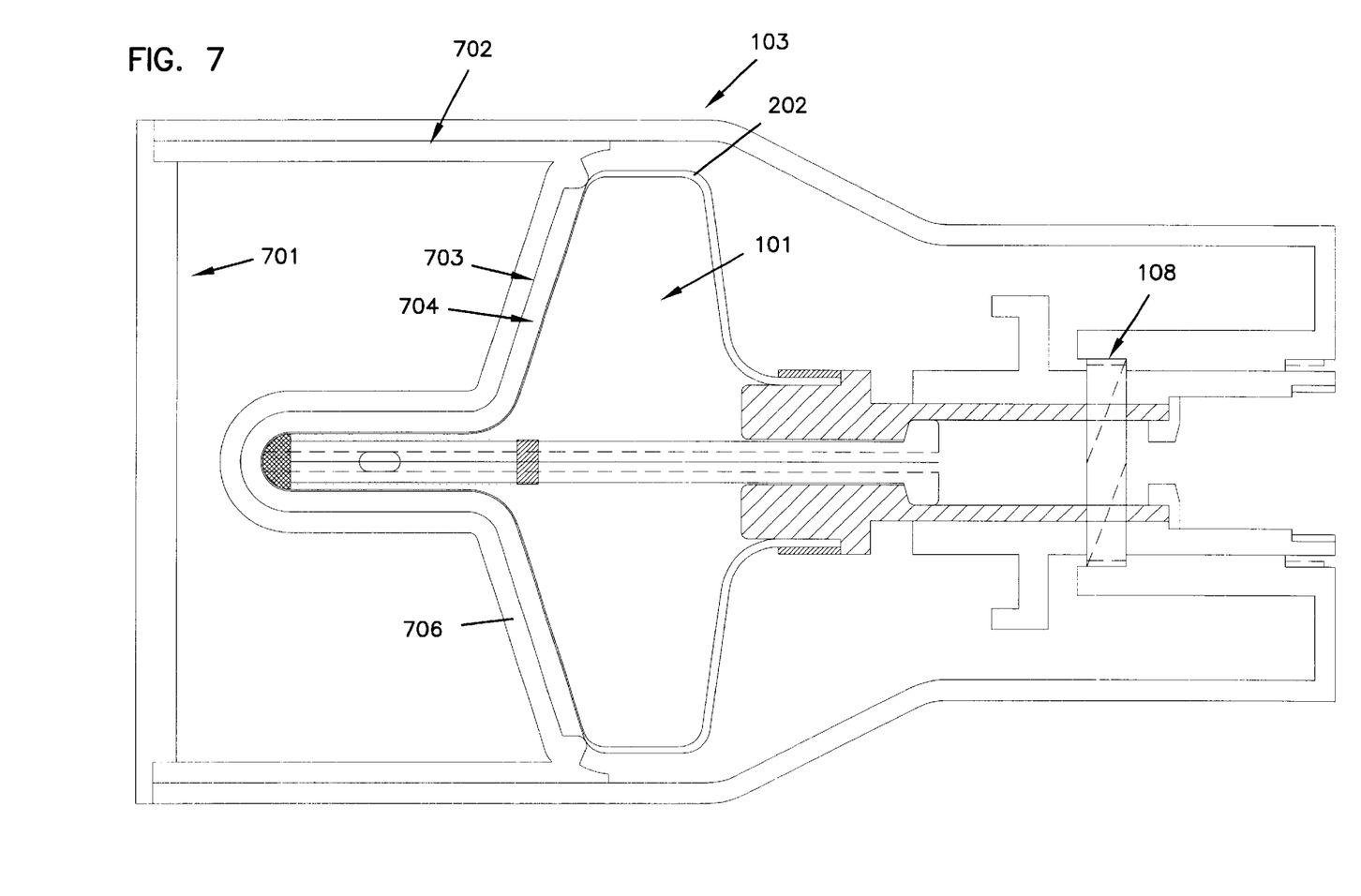
FIG. 7 is a sectional view of a plug element without fluid handling provisions.

An improved closure means is shown in FIG. 7. This closure means takes the form of a plug 701 that incorporates a guiding surface 702 that allows the plug 701 to be inserted into the container 103 without coming into contact with the sampling member 101; threads or other means not detailed for securing the plug to the container; and a surface 703 that follows, but is spaced apart from the sample containing surface contacting either the side wall 202 of the sampling member 101 or a flange not shown protruding from this side wall to form a liquid tight compartment 704 that approximately conforms to the shape of the sampling surface of the sampling member. As the enclosed volume of this compartment is substantially less than the volume of a compartment formed by a simple cap, the potential for the sample becoming air dried is significantly reduced.

More complex plugs may be implemented depending upon the manner in which the collected cellular sample is to be processed and evaluated. In most instances, it is desirable to bring the cells into contact with a liquid medium at the earliest possible time after sample collection in order to eliminate the potential for air drying and to begin the processing of the cells. A suitable plug for this instance is as is shown in FIG. 7 and described above with the addition of one or more ports 706 through which the liquid medium can be injected or otherwise introduced into and/or removed from the liquid tight compartment 704. These ports may be configured such that the fluid medium can be introduced from an external source. Alternatively, the fluid medium can be incorporated into the body of the plug.

Figure 8:
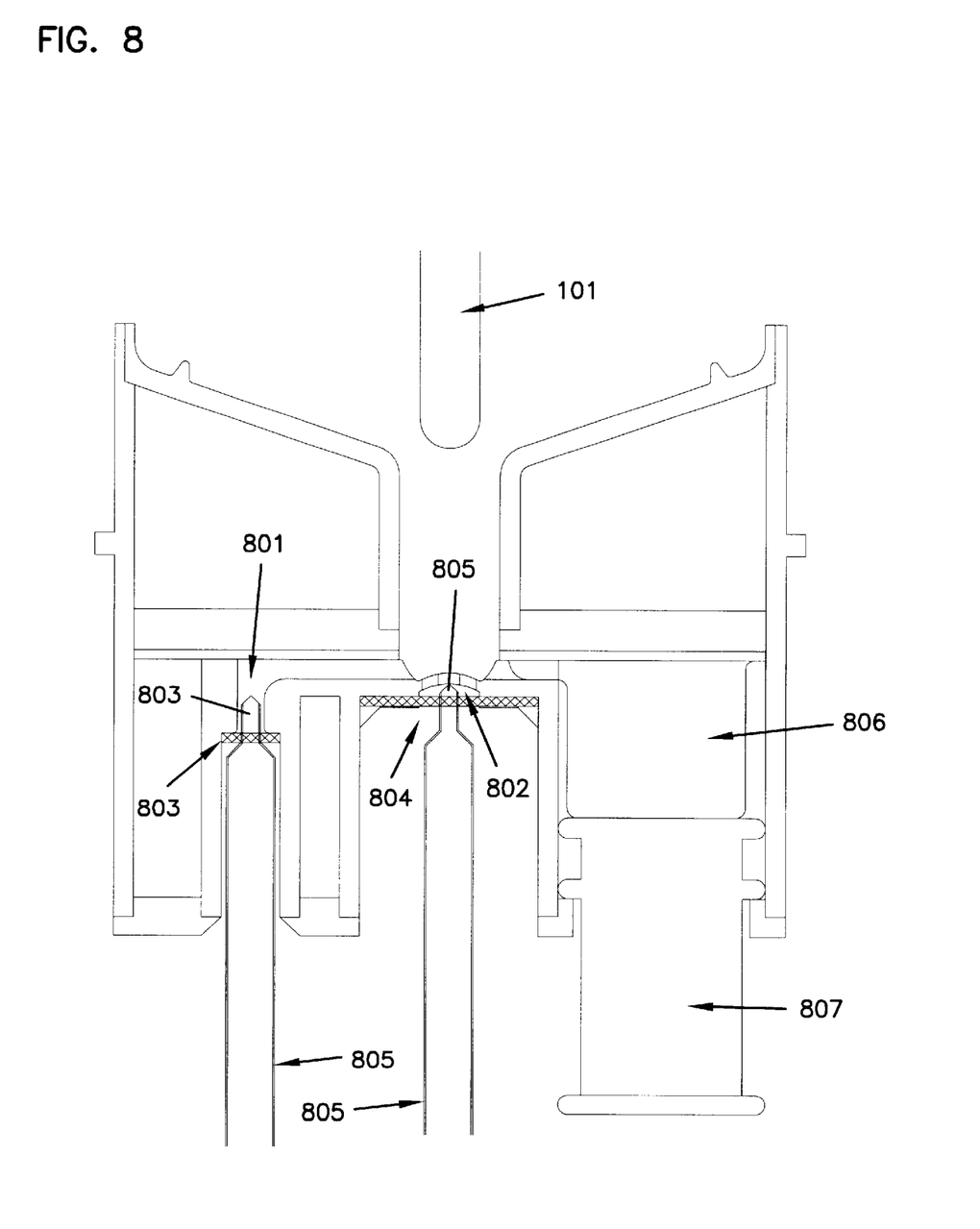
FIG. 8 is a sectional view of a plug element that incorporates fluid handling provisions as well as an internal reagent container.

An alternate embodiment of such a plug is shown in FIG. 8. This particular embodiment incorporates two externally accessible ports 801, 802 plus a compartment for a liquid medium contained within the plug body. One of the externally accessible ports 801 is intended for the introduction of an externally supplied fluid medium into the liquid tight compartment 704 while the second externally accessible port 802 is intended for the removal of the fluid from the compartment. Both ports are isolated by a sealing means shown schematically as septa 803, 804 in FIG. 8 to prevent unwanted fluid loss through these ports. This ports may be entered by probes 805 that communicate with the appropriate external fluidics. The internally contained fluid medium may be contained within a compartment within the plug not shown or within a secondary container 806 within such a compartment. The embodiment shown illustrates this secondary container as a flexible break seal pouch. Fluid is delivered from this pouch 806 into the liquid tight compartment 704 when an externally accessible plunger 807 is actuated. Although not explicitly shown in FIG. 8, the air displaced during the introduction of fluid into the fluid tight compartment is vented externally or into a compartment of the plug through holes in the wall of the plug or by air pressure displacement of the seal between the plug and the sampling member. Numerous other embodiments of these functions can be envisioned within the spirit of the present invention.

One anticipated manner of processing and evaluation is to remove the cells from the surface of the sampling member into a liquid suspension; deposit the cells from this suspension onto a microscope slide; and stain and evaluate the resulting specimen in the same manner as a conventional liquid based preparation. One suitable plug for this method of use is illustrated in FIG. 8 less the port 801 for the external introduction of the fluid medium. The fluid medium employed in this application is a cell preservative solution such as is available from commercial sources such as Cytyc Boxborough, Mass. and Tripath Imaging, Burlington, N.C.

The precise manner of use of such a plug depends upon the manner of adhesion between the collected cells and the surface of the sampling member 101. In each instance, after the plug 701 has been introduced into and secured to the container 103, the clinician actuates the plunger 807 to dispense the preservative solution into the liquid tight compartment 704 where it contacts the cells adhering to the collection surface. Certain coatings such as collagen fraction IV that may be applied to the sampling member to promote adhesion of the cells to the sampling member lose their ability to retain cells when immersed in an excess volume of a fluid medium such as the cell preservative solution. In this instance, static contact between the cell preservative solution and the surface of the sampling member is adequate to cause release of the collected cells into the fluid medium. In other instances, mechanical stimulation by, for example, shaking of the device or introduction of pulsating air pressure into the sampling member through the interface element, may be necessary in order to release the cells into suspension. In either case, the fluid medium containing the suspended cells is removed from the fluid tight compartment 704 by means of a port 802 and processed as a liquid based preparation by commercially available means such as those available from Cytyc Boxborough, Mass., Tripath Imaging Burlington, N.C., Sakura Fine Teck Torrance, Calif. and others.

Another anticipated mode of use is in conjunction with a device for the in-situ detection and evaluation of abnormal cells on the surface of the sampling member as is described in copending application 60/112,274. The specific embodiment of a plug that is applicable to this mode of use depends upon the specifics of the staining chemistry utilized in the detection process and the partitioning of functions within the detection device. One possible configuration requires that the collected cells be fixed on the surface of the sampling member before staining; that the staining protocol requires the sequential application of two different reagents to the cells; and that the cells be washed between steps in the protocol to remove excess reagent. It is further assumed, for the purposes of this example, that the fixative and both staining reagents are to be contained in the plug while the wash solution is introduced from an external source and that all processing subsequent to the introduction of the fixative will be carried out by an automated instrument.

A plug that is suitable for this mode of use is similar to that shown in FIG. 8 except that the number of reagent pouches is increased from one to three. The actuator 807 is associated with the break seal pouch 806 containing the fixative solution is designed such that it can be manually actuated by the clinician. The actuators associated with the pouches containing the staining reagents are similar to that associated with the fixative pouch except that the external protuberance has been removed. The result of this modification is that the pouches containing the staining reagents can be actuated by the processing instrument, but cannot be actuated manually.

After collection of the cells and after the plug 701 has been introduced into and secured to the container 103, the clinician actuates the plunger 807 to dispense the fixative solution into the liquid tight compartment 704 where it contacts the cells adhering to the collection surface. The entire assembly is then introduced into the processing instrument where the remaining steps of the protocol and the detection of abnormal cells are performed.

The fixative solution must remain in contact with the cells for a specified minimum period of time in order to ensure that the cells are properly conditioned for staining and that the cells remain adhered to the sampling member during processing. An instrument readable timer not shown is incorporated into the plug in order to ensure that this minimum time constraint has been met prior to the initiation of staining. This time can take the form of a fibrous body having defined and controlled fluid flow characteristics that is disposed in the wall of the plug such that one end of the fibrous body is exposed to the fluid in the fluid tight compartment while the other end is exposed in such a manner that its condition can be detected by the external instrument. Suitable fibrous bodies are available from numerous commercial sources such as Filtrona Richmond Richmond, Va.

In one embodiment of such a timer, a band of a colored or fluorescent material that is soluble in the fixative solution is applied to the fibrous body at a some distance from one end. In an alternative embodiment, a colorless or non-fluorescent material that reacts with the fixative solution to form a colored or fluorescent product is applied to the end of the fibrous body that is accessible to the external instrument. Contact of the fixative solution with the end of the fibrous body causes the fixative solution to wick along the length of the body at a controlled rate. The fluid flow properties and length of the body are selected such that the time required for the fluid front to traverse the distance between the ends of the fibrous body equals or exceeds the minimum acceptable fixation time. In the first described embodiment, the fluid front carries with it the colored or fluorescent material while, in the second embodiment, the colored or fluorescent material is formed in-situ by reaction of the fixative solution and the applied material precursor. In either case, arrival of the fluid front at the end of the body is indicated by an externally detectable change in the characteristics of the end of the fibrous body. The instrument delays initiation of the staining sequence until such a change is detected, thus ensuring that the minimum fixation time constraint has been satisfied.

The entire container-plug-sampling member assembly is oriented in the processing instrument with the plug end down. The instrument furthermore incorporates means to separate the plug 701 from the container 103 and to attach to and manipulate the sampling member 101 via the interface element 102. Processing is initiated by elevating the sampling member from its resting position relative to the plug and allowing the fixative to drain into the plug from which it is removed via the drain port 802. Wash solution is then introduced from an external source via the external fill port 801 into the well formed by the face of the plug. Note that the instrument may also introduce reagents into this well by means of a pipetting mechanism. The sampling member is lowered into the pool of wash solution and appropriately agitated to promote mixing and uniform washing. At the end of the wash period, the sampling member is raised above the pool and the wash solution is drained from the well as before. This cycle is repeated for each of the reagent addition steps in the staining protocol. At the end of the protocol, the processed sampling member is raised above the pool and dried prior to the detection process. The sampling member can be inflated prior to the detection process.

After detection is complete, the plug, container and sampling member are reassembled by the instrument and delivered to the user for disposal or further processing. This further processing can take the form of treating the cells adhering to the sampling membrane with a Pap or other stain that allows visual evaluation of the cells in-situ on the sampling member, or alternatively to release the cells into suspension for further evaluation as a liquid based preparation according to procedures that are analogous to those described previously.

While the invention has been described with reference to specific embodiments, it will be apparent to those skilled in the art that many alternatives, modifications and variations may be made. Accordingly, the present invention is intended to embrace all such alternatives, modifications and variations that may fall within the spirit and scope of the appended claims.

We claim:

1. A cervical cell collector comprising:

sampling means for sampling a cervix in a spatially resolved manner, the sampling means comprising a pliable balloon that, when inflated, has a sampling surface configured to match a mirror image of an outer portion of the cervix;

supporting means for supporting the sampling means; and inflation means for reversibly inflating and deflating the sampling means;

wherein the pliable balloon comprises an inner chamber and an outer chamber to allow for controlled inflation and deflation of different portions of the sampling surface.

2. A cervical cell collector comprising:

a sampling member comprising an inner balloon and an outer balloon; and an elongate handle removably attachable to the sampling member;

wherein the sampling member comprises a non-planar surface configured to approximate a mirror image of an exterior of a human cervix.

3. The cervical cell collector of claim 2, wherein the inner balloon can be reversibly inflated.

4. The cervical cell collector of claim 2, wherein the outer balloon comprises the non-planar surface configured to approximate the exterior shape of the human uterus.

* * * * *

UNITED STATES PATENT AND TRADEMARK OFFICE
CERTIFICATE OF CORRECTION

PATENT NO. : 6,475,164 B2
DATED : November 5, 2002
INVENTOR(S) : Gombrich et al.

Page 1 of 1

It is certified that error appears in the above-identified patent and that said Letters Patent is hereby corrected as shown below:

Column 2,
Lines 39-49, should read as follows:

-- The manner in which a positive result is followed up varies substantially by country. In some countries such as the US, a finding of ASCUS (atypical squamous cells undetermined significance) or higher is generally considered to be grounds for follow-up or medical intervention. In other countries, the standard of care is to follow up or intervene in cases where the detected degree of abnormality corresponds to LSIL (low-grade squamous intraepithelial lesions) or HSIL (high-grade squamous intraepithelial lesions) and higher, but, in recognition that many lower grade abnormalities are benign or revert to normal over time, to ignore lower grade detected abnormalities. It is therefore desirable to be able to establish a reporting threshold that is consistent with the prevailing standard of care. --

Column 9,
Line 3, please insert the following omitted paragraph:

-- Further protection of the collected sample is obtained by applying some form of closure to the open end of the container 103. Numerous forms of closure can be employed for this purpose. The simplest form of closure is a cap that can be applied to the open end of the container and preferably retained in position by friction, a snap feature or other similar means. The use of a simple cap, however, allows the possibility that the collected cellular sample may air dry and thus become unsuitable for evaluation. --

Signed and Sealed this

Twenty-seventh Day of July, 2004

JON W. DUDAS
*Acting Director of the United States Patent and Trademark Office*